United States Patent
Javidi et al.

(10) Patent No.: US 7,616,320 B2
(45) Date of Patent: Nov. 10, 2009

(54) METHOD AND APPARATUS FOR RECOGNITION OF MICROORGANISMS USING HOLOGRAPHIC MICROSCOPY

(76) Inventors: Bahram Javidi, 54 Ellise Rd., Storrs, CT (US) 06268; Yeom Seokwon, 12-1406 Sampoong APT Seocho 4 dong, Seochogu, Seoul (KR) 137-074; Edward Carapezza, 336 Woodville Rd., Ashaway, RI (US) 02804; Inkyu Moon, 141 Courtyard La., Storrs-Mansfield, CT (US) 06268

( * ) Notice: Subject to any disclaimer, the term of this patent is extended or adjusted under 35 U.S.C. 154(b) by 343 days.

(21) Appl. No.: 11/470,865

(22) Filed: Sep. 7, 2006

(65) Prior Publication Data
US 2007/0216906 A1    Sep. 20, 2007

Related U.S. Application Data

(60) Provisional application No. 60/782,484, filed on Mar. 15, 2006.

(51) Int. Cl.
*G01B 9/021* (2006.01)
(52) U.S. Cl. ..................................... 356/457
(58) Field of Classification Search ................ 356/457, 356/458, 521
See application file for complete search history.

(56) References Cited

FOREIGN PATENT DOCUMENTS

WO    WO2004 086941 A2    10/2004

OTHER PUBLICATIONS

Javidi et al, "Three-dimensional imaging and recognition of microorganism using single-exposure on-line (SEOL) digital holography" $13^{th}$ Jun. 2005, Optics Express, vol. 13, No. 12, pp. 4492-4506.*
Three-dimensional imaging and recognition of microorganisms using single-exposure on-line (SEOL) digital holography, Bahram Javidi, Inkyu Moon, Seokwon Yeom, and Edward Carapezza, Optics Express, vol. 13, No. 12, Jun. 13, 2005.

* cited by examiner

*Primary Examiner*—Patrick J Connolly
(74) *Attorney, Agent, or Firm*—Cantor Colburn LLP

(57) ABSTRACT

Disclosed herein is a method that relates to identifying a microorganism. The method comprising, diffracting laser light through a microorganism, combining a reference beam with the diffracted light on a single axis, and recording the combined light holographically as a three-dimensional image with a single exposure on a detector array. The method further comprising, reconstructing the holographic image and matching the reconstructed image with reference images of known microorganisms. Further disclosed herein is an apparatus for identifying a microorganism. The apparatus comprising, an interferometer to record an image of an unknown microorganism using single-exposure on-line (SEOL) digital holography, a means for reconstructing the recorded image, and a means for matching the reconstructed image with images of known microorganism.

20 Claims, 10 Drawing Sheets

METHOD AND APPARATUS FOR RECOGNITION OF MICROORGANISMS USING HOLOGRAPHIC MICROSCOPY

CROSS REFERENCE TO RELATED APPLICATION

This application claims priority to U.S. provisional application, 60/782,484, filed Mar. 15, 2006, the entire contents of which are incorporated herein by reference.

BACKGROUND

Optical information systems have proven to be very useful in the design of two-dimensional (2D) pattern recognition systems. Recently, interest in three-dimensional (3D) optical information systems has increased because of its vast potential in applications such as object recognition, image encryption as well as 3D display. Digital holography is attractive for visualization and acquisition of 3D information for these various applications. In digital holography, 3D complex (magnitude and phase) information can be reconstructed at arbitrary depths and perspectives. The 3D complex information might provide more discriminant features for the recognition of microorganisms.

Identification and recognition of microorganisms is desirable for several applications. It may be used to diagnose an infection caused by specific bacteria or detect biological weapons for security and defense, for example. It may also be used for monitoring plankton in the ocean. Quantification of microorganisms may be useful information for wastewater treatment facilities.

Several challenges accompany the automatic recognition of living organisms, such as; they are not rigid objects, they vary in size and shape, and they can move, grow, and reproduce themselves depending on growth conditions. Bacteria and algae, in particular, have relatively simple morphological traits, however they are very tiny and there exist many variants among the same species. Additionally, they may occur as a single cell or form an association of various complexities according to environmental conditions.

One method that can be considered for 3D complex information with for identification and recognition of microorganisms is off-axis digital holography since it requires only a single exposure in separating the original image from the undesired DC and conjugate images. However, off-axis digital holography has a number of drawbacks. Only a fraction of the space-bandwidth product of the photo sensor is used to reconstruct the 3D image, which results in substantially reduced quality of visualization and compromises resolution. As a result, it reduces the accuracy of object recognition. In addition, the angle between the object beam and reference beam during the holographic synthesis is a function of the reconstructed image size, which creates problems in monitoring dynamic scenes containing living objects.

Another identification and recognition method that has undergone study in an attempt to overcome these problems is phase-shifting on-line digital holography. This technique requires multiple interferogram recordings with phase shifts in the reference beam. The multiple exposures are used to remove the DC and the conjugate images in the interferogram and the Fresnel diffraction field of the 3D object is obtained. However, this procedure is not suitable for dynamic events such as moving 3D microorganism and is sensitive to external noise factors such as environmental vibration and fluctuation.

Accordingly, there is a need in the art to overcome the aforementioned problems of existing techniques for microorganism identification and recognition.

BRIEF DESCRIPTION OF THE INVENTION

Disclosed herein is a method that relates to identifying a microorganism. The method comprising, diffracting laser light through a microorganism, combining a reference beam with the diffracted light on a single axis, and recording the combined light holographically as a three-dimensional image with a single exposure on a detector array. The method further comprising, reconstructing the holographic image and matching the reconstructed image with reference images of known microorganisms.

Further disclosed herein is a method that relates to recognizing a microorganism. The method comprising, recording three-dimensional complex morphologies of a microorganism with single-exposure on-line (SEOL) digital holography, reconstructing the recorded image digitally, and matching the reconstructed three-dimensional complex morphologies with three-dimensional complex morphologies of known microorganisms.

Further disclosed herein is an apparatus for identifying a microorganism. The apparatus comprising, an interferometer to record an image of an unknown microorganism using single-exposure on-line (SEOL) digital holography, a means for reconstructing the recorded image, and a means for matching the reconstructed image with images of known microorganism.

Further disclosed herein is a computer program product that relates to identifying an image of a microorganism in a computer environment. The computer program product comprising, a storage medium readable by a processing circuit and storing instructions for execution by the processing circuit for facilitating a method. The method comprising, receiving an image of a microorganism from a detector array of a single-exposure on-line (SEOL) digital holography system, digitally storing the image, reconstructing the image digitally, and matching the reconstructed image with reference images of known microorganisms.

BRIEF DESCRIPTION OF THE FIGURES

Referring now to the figures, which are exemplary embodiments and should not be construed to be limiting in any way, and wherein like elements are numbered alike.

DETAILED DESCRIPTION OF THE INVENTION

Embodiments of the invention may provide real-time 3D visualization, monitoring and recognition of microorganisms using single-exposure on-line (SEOL) digital holography. A benefit of embodiments of the invention may be that 3D information of microorganisms is recorded, which provides the various slices of the complex images of microorganism, which are numerically reconstructed at arbitrary depths and perspectives.

SEOL holography can be used for dynamic events because it requires only a single-exposure. Another benefit of SEOL digital holography for monitoring of a 3D dynamic time varying scene is that 3D scenes can be numerically focused without mechanical focusing as is required by conventional microscopy.

Figure 1:
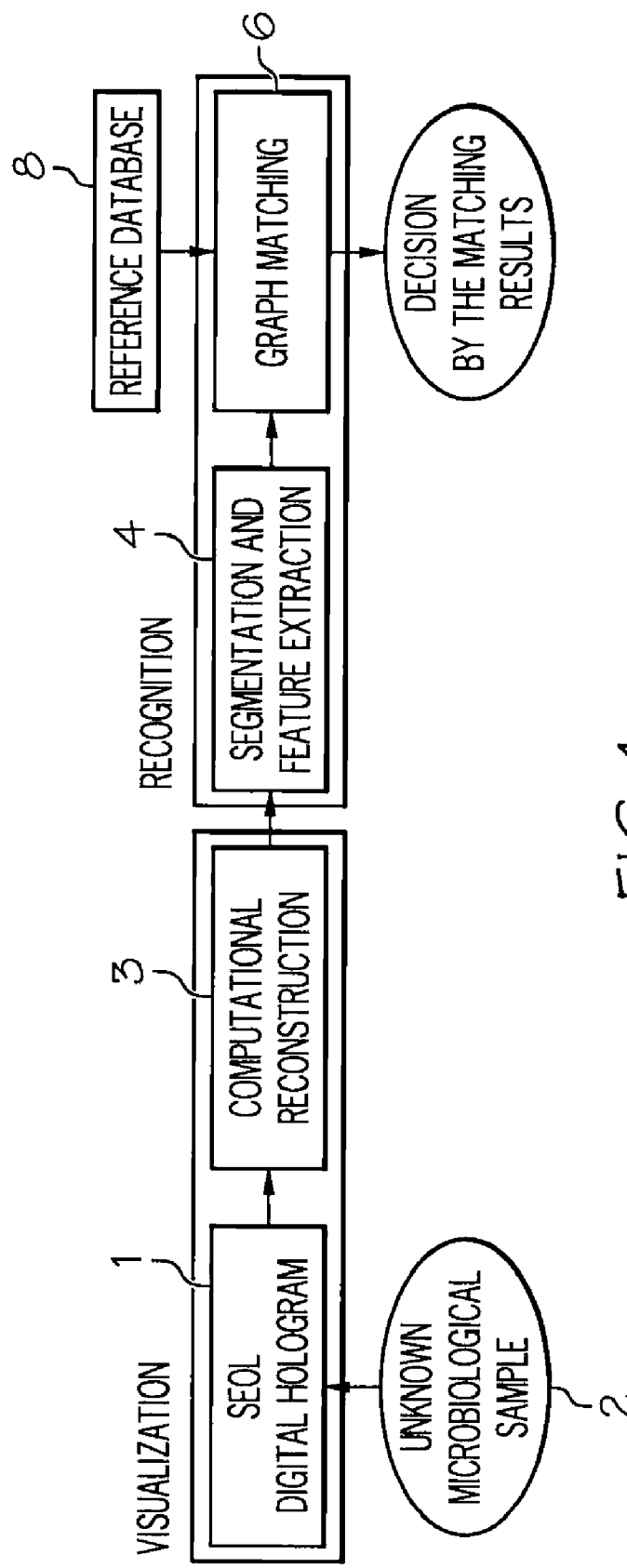
FIG. 1 depicts a block diagram of a system in accordance with an embodiment of the invention.

Referring to FIG. 1, a block diagram depicts the frameworks of the system composed of several stages. At the first stage, a SEOL digital holographic system 1 performs 3D imaging of an unknown microorganism sample 2. Utilizing a Mach-zehnder interferometer, the system opto-electronically records the complex wave at a single plane in a digital hologram. The complex wave is transmitted from the microorganisms 2 by Fresnel diffraction. The recorded Fresnel diffraction field can be used to reconstruct the complex amplitude image of microorganisms at an arbitrary depth plane. Reconstructed images 3 are resized and objects of interest are segmented and features are extracted at the segmentation and extraction stage 4. Foreground objects are segmented using a histogram analysis. Gabor-based wavelets extract salient features by decomposing complex information of microorganisms in the spatial frequency domain.

A graph matching stage 6, which is next, involves rigid graph matching (RGM). RGM is a feature matching technique to search for and identify 3D complex morphologies that match reference shapes or graphs from a reference database 8. The reference graph representing the reference shape is predetermined in a database 8. The reference shape represents unique morphological features of a referred microorganism and potentially matching unknown microorganism samples. During RGM, the reference database 8 is searched for shapes that have similar morphological features to those of the unknown microorganism by measuring similarities and differences between feature vectors. The feature vectors are defined at the nodes of two identical graphs on the reference images from the database 8 and the reconstructed (unknown input) images 3, respectively. The RGM combined with Gabor-based wavelets has proven to be a robust template matching technique that is invariant to shift, rotation, and distortion.

Single Exposure On-Line (SEOL) Digital Holography

Figure 2:
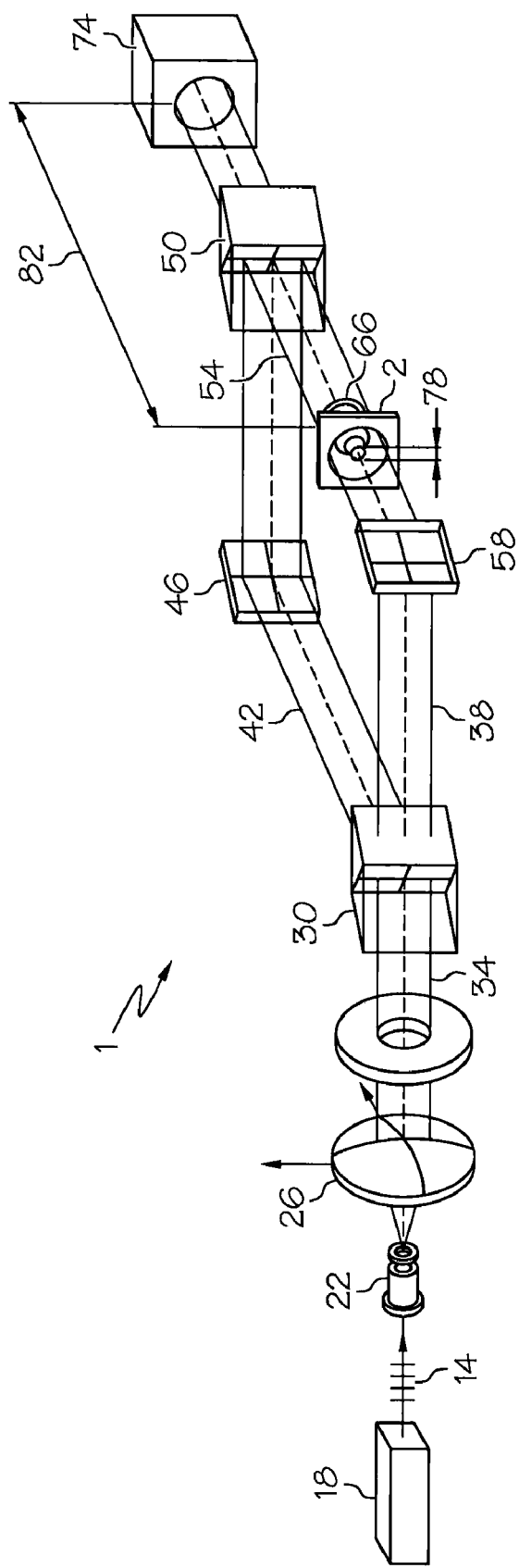
FIG. 2 depicts a three-dimensional single-exposure on-line digital holographic optical monitoring system in accordance with an embodiment of the invention.
Figure 3:
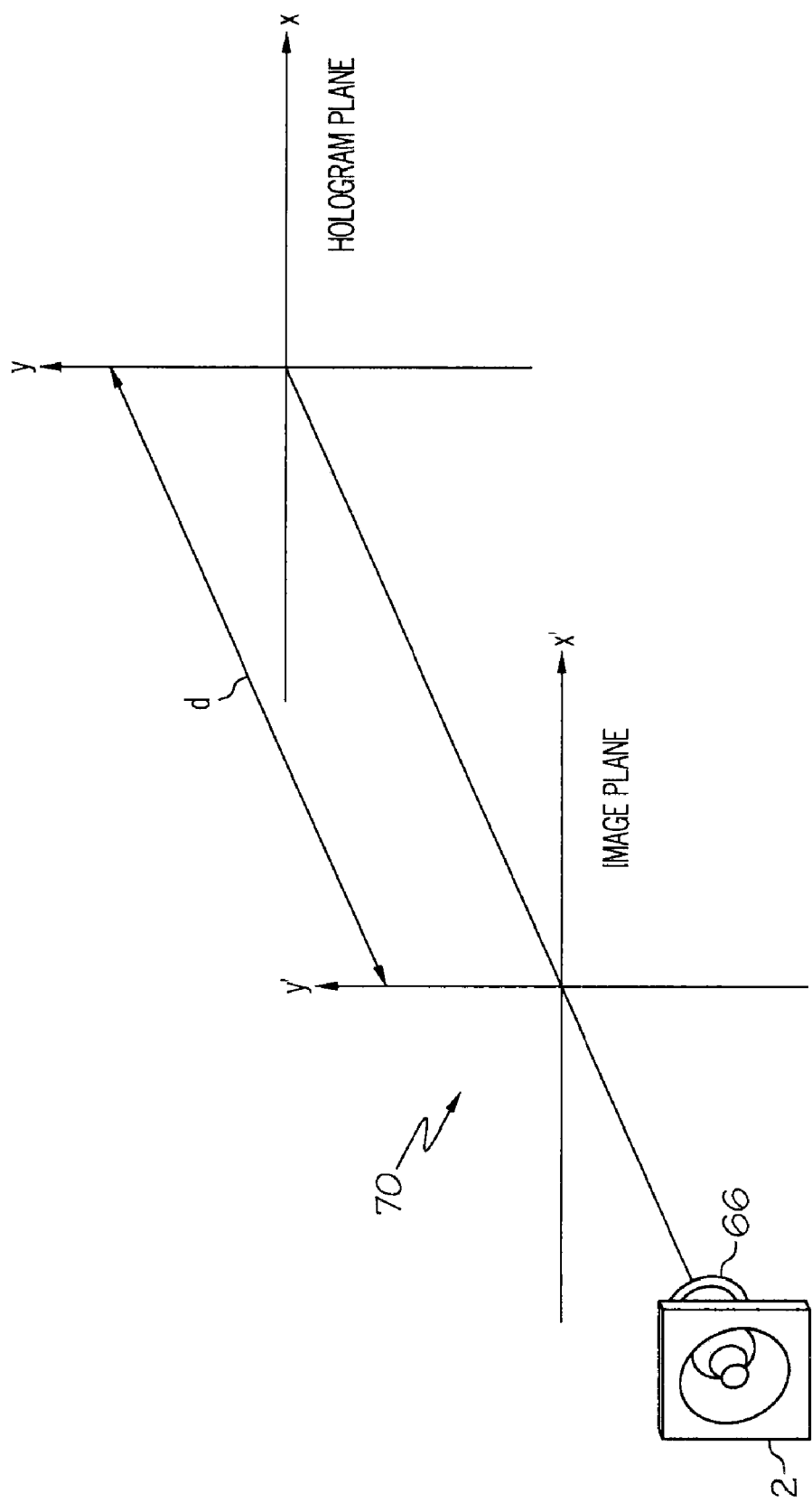
FIG. 3 illustrates the relationship of an image plane to a hologram plane in accordance with an embodiment of the invention.

Referring to FIG. 2, a 3D optical monitoring system 1 using a SEOL digital holographic recording setup is depicted. Polarized light 14 from an Argon laser 18 with a center wavelength ($\lambda$) of 514.5 nm, is expanded by use of a spatial filter 22 and a collimating lens 26 to provide spatial coherence. A first beam splitter 30 divides an expanded beam 34 into an object beam 38 and a reference beam 42. The reference beam 42 reflects off a first mirror 46 and then a second beam splitter 50 where it is combined with diffracted light 54 the source of which will now be discussed. The object beam 38 reflects off a second mirror 58 and illuminates a microorganism sample 2 and the microscope objective 66 produces a magnified image positioned at the image plane 70 of the microscope (see FIG. 3). The reference beam 42 and the diffracted light 54 from the microorganism sample 2 combine as they pass through the second beam splitter 50 to form an on-axis interference pattern that is recorded by a charge-coupled device (CCD) camera 74. This system uses no optical components for the phase retardation in the reference beam, which the phase-shifting digital holography technique requires. Also, only a single exposure is recorded in the optical monitoring system 1 described above.

Following are descriptions of both, on-axis phase-shifting digital holography and SEOL. In on-axis phase-shifting digital holography, a hologram recorded on a CCD can be represented as follows:

$$H_p(x, y) = [A_H(x, y)]^2 + A_R^2 + 2A_H(x, y)A_R \times \cos[\Phi_H(x, y) - \phi_R - \Delta\phi_p], \quad (1)$$

where $A_H(x, y)$ and $\Phi_H(x, y)$ are the amplitude and phase, respectively, of the Fresnel complex-amplitude distribution of the micro objects at the recording plane generated by the object beam; $A_R$ is the amplitude of the reference distribution; $\phi_R$ denotes the constant phase of the reference beam; and $\Delta\phi_p$, where the subscript p is an integer from 1 and 4, denoting the four possible phase shifts required for on-axis phase-shifting digital holography. The desired Fresnel wave function of the biological object, $A_H(x, y)$ and $\Phi_H(x, y)$ can be obtained by use of the four interference patterns with different phase shifts $\Delta\phi_p = 0, \pi/2, \pi$ and $3\pi/2$.

In this description, phase-shifting on-axis digital holography with double exposure, and SEOL digital holography are implemented to obtain experimental results for the visualization and recognition of 3D biological objects. The SEOL results are compared with multiple expose phase-shifting digital holographic results. The double-exposure method requires 1) two interference patterns that have a $\pi/2$ phase difference, 2) the information about a reference beam, and 3) information about the diffracted biological object beam intensity. The complex amplitude of the microscopic 3D biological object wave at the hologram plane from the double-exposure method is represented by:

$$U_h(x, y) = A_H(x, y) \times \cos[\Phi_H(x, y)] + jA_H(x, y) \times \sin[\Phi_H(x, y)] = \{H_1(x, y) - A_H(x, y)^2 - A_R^2\}/(2A_R) + j\{H_2(x, y) - A_H(x, y)^2 - A_R^2\}/(-2A_R), \quad (2)$$

where $H_1(x, y)$ and $H_2(x, y)$ can be obtained from Equation (Eq.) (1). It is assumed that the recording between two holograms, $H_1$ and $H_2$, is uniform and reference beam is plane wave. The former assumption requires a stable recording environment and stationary objects.

SEOL digital holography is suitable for recording fast varying dynamic events. It needs to record only one hologram to gain information about the complex amplitude of the 3D biological object. The information about the wave front of a 3D biological object contained in the SEOL digital hologram is represented by the following term:

$$U_H(x, y) = 2A_H(x, y)A_R \times \cos(\Phi_H(x, y) - \phi_R) = H_1(x, y) - |A_H(x, y)|^2 - A_R^2. \quad (3)$$

In Eq. (3), $H_1(x, y)$ can be obtained from Eq. (1). To remove DC terms in Eq. (3), the reference beam intensity $|A_R|^2$ is removed by only a one time measurement in the experiment. The object beam intensity $|A_H(x, y)|^2$ can be considerably reduced by use of signal processing (for example, an averaging technique). Even though SEOL digital holography originally contains a conjugate image, the conjugate image in the interferogram can be used in recognition experiments since it has information about the biological object. Thus, the 3D biological object wave function $U_{h'}(x, y)$ including a conjugate component in Eq. (3) can be obtained by use of SEOL digital holography. It will be shown that $U_{h'}(x, y)$ in Eq. (3) obtained by a SEOL hologram can be used for 3D biological object recognition and 3D image formation. The results will be compared with that of $U_h(x, y)$ in Eq. (2) obtained by on-line phase-shifting holography, which requires multiple recordings. The microscopic 3D biological object can be restored by Fresnel propagation of $U_{h'}(x, y)$ which is the biological object wave information in the hologram plane. 3D section images can be numerically reconstructed on any parallel plane perpendicular to the optical axis by computing the following Fresnel transformation with a 2D FFT algorithm:

$$U_{o'}(m', n') = \exp\left[-j\frac{\pi}{\lambda d}(\Delta X^2 m'^2 + \Delta Y^2 n'^2)\right] \times$$
$$\sum_{m=1}^{N_x}\sum_{n=1}^{N_y} U_{h'}(m, n)\exp\left[-j\frac{\pi}{\lambda d}(\Delta x^2 m^2 + \Delta y^2 n^2)\right]$$
$$\exp\left[j2\pi\left(\frac{mm'}{N_x} + \frac{nn'}{N_y}\right)\right], \quad (4)$$

where $N_x$ and $N_y$ are the size of the $U_{h'}(m,n)$ in the x and y directions; $U_{o'}(m',n')$ and $(\Delta X, \Delta Y)$ are the reconstructed complex amplitude distribution which is called "holographic image" and resolution at the image plane, respectively; $U_{h'}(m,n)$ and $(\Delta x, \Delta y)$ are the object wave function including a conjugate component and resolution at the hologram plane, respectively; and d represents the distance between the image plane and hologram plane (see FIG. 3).

Segmentation

A description of the segmentation of digitally reconstructed holographic images follows. Since the coherent light is scattered by the semi-transparent objects, the intensity may appear in the background diffraction field. Therefore, for recognition, it is more efficient to filter out unnecessary background from computationally reconstructed holographic images.

In some embodiments of the invention, the threshold for the segmentation is obtained by using histogram analysis and the maximum transmission rate. The segmented image (o) is defined as:

$$o(m, n) = \begin{cases} o'(m, n) & \text{if } o'(m, n) < I_s \\ 0 & \text{otherwise} \end{cases}, \quad (5)$$

where $o'(m,n)$ is the intensity of the holographic image. The threshold $I_s$ is decided from the histogram analysis and the maximum transmission rate:

$$I_s = \min\lfloor \tau_{\kappa_{min}}, r_{max} \cdot \max(o') \rfloor, \quad (6)$$

where $r_{max}$ is the maximum transmission rate of coherent light after scattering by the microorganisms. The threshold $\tau_{\kappa_{min}}$ is a minimum value satisfying the following equation:

$$P_s \leq \frac{1}{N_T}\sum_{i=1}^{\kappa_{min}} h(\tau_i), \quad (7)$$

where $P_s$ is a predetermined probability; $N_T (=N_x \times N_y)$ is the number of pixels; $h(\tau_i)$ is the histogram, i.e., the number of pixels of which intensity is between $\tau_{i-1}$ and $\tau_i$; $\tau_i$ is the i-th quantized intensity level; and $\kappa_{min}$ is the minimum number of pixels that satisfies Eq. (7). For the enclosed data, the total number of intensity levels is set at 256. $P_s$ and $r_{max}$ can be decided according to the prior knowledge of the spatial distribution and transmittance of the microorganisms.

Gabor-Based Wavelets and Feature Vector Extraction

Provided here is a brief review of Gabor-based wavelets and present feature vectors. Gabor-based wavelets are composed of multi-oriented and multi-scaled Gaussian-form kernels that are suitable for local and global spectral analysis.

Gabor-Based Wavelets

Gabor-based wavelets have the form of a Gaussian envelope modulated by the complex sinusoidal functions. The impulse response (or kernel) of the Gabor-based wavelet is:

$$g(x) = \frac{|k|^2}{\sigma^2}\exp\left(-\frac{|k|^2|x|^2}{2\sigma^2}\right)\left[\exp(jk \cdot x) - \exp\left(-\frac{\sigma^2}{2}\right)\right], \quad (8)$$

where x is a position vector, k is a wave number vector, and σ or is proportional to the standard deviation of the Gaussian envelope. By changing the magnitude and direction of the vector k, the Gabor kernel can be scaled and rotated to make self-similar forms.

It is possible to define a discrete version of the Gabor kernel as $g_{uv}(m,n)$ at $k=k_{uv}$ and $x=[m\ n]^t$, where m and n are discrete coordinates in 2D space in the x and y directions, respectively. Sampling of k is done as $k_{uv}=k_{Ou}[\cos\phi_v \sin\phi_v]^t$, $k_{Ou}=k_0/\delta^{u-1}$, and $\phi_v=[(v-1)/V]\pi$, $u=1, \ldots, U$ and $v=1, \ldots, V$, where $k_{Ou}$ is the magnitude of the wave number vector; $\phi_v$ is the azimuth angle of the wave number vector; $k_0$ is the maximum carrier frequency of the Gabor kernels; δ is the spacing factor in the frequency domain; u and v are the indexes of the Gabor kernels; U and V are the total numbers of decompositions along the radial and tangential axes, respectively; and t stands for the matrix transpose.

The Gaussian-envelope in the Gabor-filter achieves the minimum space-bandwidth product. Therefore, it is suitable to extract local features with high frequency bandwidth (small u) kernels and global features with low frequency bandwidth (large u) kernels. It is noted that the Gabor-based wavelet has strong response to the edges if the wave number vector k is perpendicular to the direction of edges.

Feature Vector Extraction

Let $h_{uv}(m,n)$ be the filtered output of the image $o(m,n)$ after it is convolved with the Gabor kernel $g_{uv}(m,n)$:

$$h_{uv}(m, n) = \sum_{m'=1}^{N_x} \sum_{n'=1}^{N_y} g_{uv}(m - m', n - n')o(m', n'), \quad (9)$$

where $o(m,n)$ is the normalized image between 0 and 1 after the segmentation; and $N_x$ and $N_y$ are the size of reconstructed images in the x and y directions, respectively. $h_{uv}(m,n)$ is also called the "Gabor coefficient."

A feature vector defined at a pixel (m,n) is composed of a set of the Gabor coefficients and the segmented image. The rotation-invariant property can be achieved simply by adding up all the Gabor coefficients along the tangential axes in the frequency domain. Therefore, a rotation-invariant feature vector v is defined as:

$$v(m, n) = \left[ o(m, n) \sum_{v=1}^{V} h_{1v}(m, n) \cdots \sum_{v=1}^{V} h_{Uv}(m, n) \right]^t. \quad (10)$$

Therefore, the dimension of a feature vector v is U+1. In the experiments, only real parts of the feature vector are used since they are more suitable to recognize filamentous structures. There is no optimal way to choose the parameters for the Gabor kernels, but several values are widely used heuristically depending on the applications. The parameters are set up at $\sigma=\pi$, $k_0=\pi/2$, $\delta=2\sqrt{2}$, U=3, V=6 in this example.

Rigid Graph Matching (RGM)

Originally, the RGM is part of a dynamic link association (DLA) to allow elastic deformation of the graph. However, the rigid graph matching part has only been adopted for microscopic analysis here. The RGM realizes a robust template-matching between two graphs that is tolerant to translation, rotation, and distortion caused by noisy data.

The graph is defined as a set of nodes associated in the local area. Let R and S be two identical and rigid graphs placed on the reference ($o_r$) object and unknown input image ($o_S$), respectively. The location of the reference graph R is predetermined by the translation vector $p_r$ and the clockwise rotation angle $\theta_r$. A position vector of the node k in the graph R is:

$$x_k^r = A(\theta_r)(x_k^o - x_c^o) + p_r, \quad k=1, \ldots, K, \quad (11)$$

-continued $$A(\theta) = \begin{bmatrix} \cos\theta & \sin\theta \\ -\sin\theta & \cos\theta \end{bmatrix}, \quad (12)$$

where $x_k^o$ and $x_c^o$ are, respectively, the position of the node k and the center of the graph which is located at the origin without rotation; K is the total number of nodes in the graph; and A is a rotation matrix.

Assuming the graph R covers a designated shape of the representing characteristic in the reference microorganism, a search is performed of the similar local shape by translating and rotating the graph S on unknown input images. Any rigid motion of the graph S is described by translation vector p and clock wise rotation angle θ:

$$x_k^S(\theta,p)=A(\theta)(x_k^o-x_c^o)+p, \ k=1,\ldots,K, \quad (13)$$

where $x_k^S$ is a position vector of the node k in the graphs S. The transformation in Eq. (13) allows robustness in detection of rotated and shifted reference morphologies.

A similarity function between the graph R and S is defined as:

$$\Gamma_{rs} = \frac{1}{K} \sum_{k=1}^{K} \gamma_k(\theta, p), \quad (14)$$

where the similarity at one node is the normalized inner product of two feature vectors:

$$\gamma_k(\theta, p) \equiv \frac{\langle v[x_k^r], v[x_k^s(\theta, p)] \rangle}{\|v[x_k^r]\| \|v[x_k^s(\theta, p)]\|}, \quad k = 1, \ldots, K. \quad (15)$$

In Eq. (15), ⟨⟩ stands for the inner product of two vectors; and $v[x_k^r]$ and $v[x_k^S(\theta,p)]$ are feature vectors defined at $x_i^r$ and $x_k^S(\theta, p)$, respectively.

A difference cost function to improve discrimination capability of two graphs R and S is defined as:

$$C_{rs} = \frac{1}{K} \sum_{k=1}^{K} c_k(\theta, p), \quad (16)$$

where the cost at one node is the norm of difference of two feature vectors:

$$c_k(\theta, p) = \|v[x_k^r k] - v[x_k^S(\theta, p)]\|, \ k=1,\ldots,K. \quad (17)$$

To utilize the depth information of the SEOL hologram, multiple references are simultaneously used. The similarity function $\Gamma_{r_j s}^j (\theta_j; p)$ and the difference cost $C_{r_j s} (\theta_j; p)$ are measured by the feature vectors between the graph R on the image $o_{r_j}$ and the graph S on the image $o_S$. The graph R covers the fixed region in the reference images, "$o_{r_j}$" j=1, . . . ,J; J is the total number of reference images reconstructed at different depths.

The graph S is identified with the reference shape which is covered by the graph R if two conditions are satisfied as follows:

Accept detection at p if $\Gamma_{r_js}(\hat{\theta}_j; p) > \alpha_\Gamma$ and $C_{r_js}(\hat{\theta}_j; p) < \alpha_C$, (18)

$$\hat{j} = \max_j \lfloor \Gamma_{r_1s}(\hat{\theta}_1; p), \ldots, \Gamma_{r_js}(\hat{\theta}_J; p) \rfloor,$$ (19)

where $\hat{j}$ is the index of the reference image which produces the maximum similarity between the graph R and the graph S with the translation vector p and the rotation angle $\hat{\theta}_j$; $\alpha_\Gamma$ and $\alpha_C$ are thresholds for the similarity function and the difference cost, respectively; and $\hat{\theta}_j$ is obtained by searching the best matching angle to maximize the similarity function:

$$\hat{\theta}_j = \underset{\theta}{\operatorname{argmax}} \Gamma_{r_js}(\theta, p).$$ (20)

Referring back to FIG. 1, a majority of the stages depicted may be performed with a computer. For example, the recording of the image of the unknown microorganism may be received and recorded by a computer. The computational reconstruction 3 of the image may be performed digitally as well as the segmentation and feature extraction 4. The computer may also retrieve reference images from the reference database 8 and carryout the graph matching 6 and the reporting of the matching results.

Results from an Embodiment of the Invention

Experimental results of visualization and recognition of two filamentous algae (sphacelaria alga and tribonema aequale alga) specifically, in accordance with an embodiment of the invention will be reviewed. However, the scope of the invention is not limited to this example. First, 3D imaging of algae using SEOL holography compared with phase-shifting on-line digital holography is presented. Second, a recognition process using feature extraction and graph matching are presented to localize the predefined shapes of two different microorganisms.

3D Imaging with SEOL Digital Holography

Figure 4A:
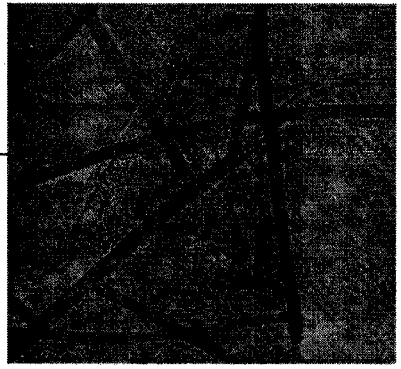
FIG. 4*a* depicts a 2 dimensional image of sphacelaria.
Figure 4B:
FIG. 4*b* depicts a digital hologram (magnitude part) by single-exposure on-line (SEOL) digital holography technique.
Figure 4C:
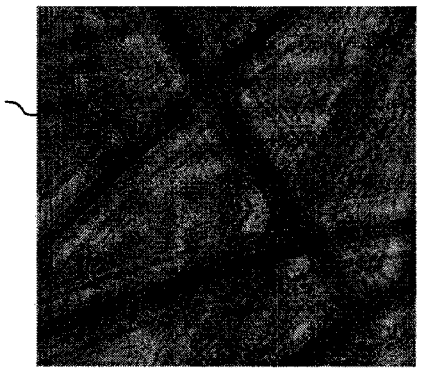
FIG. 4*c* depicts a reconstructed image (magnitude part) of sphacelaria using SEOL digital holography at distance d=180 mm.
Figure 4D:
FIG. 4*d* depicts a reconstructed image (magnitude part) of sphacelaria using SEOL digital holography at distance d=190 mm.
Figure 4E:
FIG. 4e depicts a reconstructed image (magnitude part) of sphacelaria using phase-shifted on-line digital holography at distance d=190 mm.
Figure 4F:
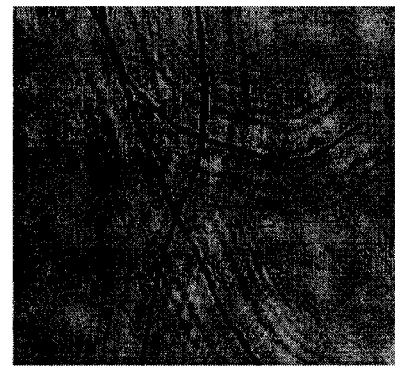
FIG. 4f depicts a reconstructed image (magnitude part) of tribonema aequale using SEOL digital holography at distance d=180 mm.

This subsection compares the 3D algae visualization of the SEOL digital holography with that of the multiple-exposure phase-shifting on-line digital holography by experiments. In the experiments presented here, the images are reconstructed from digital holograms with 2048×2048 pixels and a pixel size of 9 μm×9 μm. The microorganisms are sandwiched between two transparent cover slips. The diameter 78 of the sample 2 is around 10~50 μm. Two holograms for the alga samples are generated. The microscopic 3D biological object was placed at a distance 82 from the CCD array 74 of 500 mm as shown in FIG. 2. The results of the reconstructed images from the hologram of the alga samples are shown in FIG. 4(a)-4(f). FIGS. 4(a) and (b) show sphacelaria's 2D image 86 and the digital hologram 90 by SEOL digital holography technique, respectively. FIGS. 4(c) and (d) are sphacelaria's reconstructed images from the blurred digital holograms at distance of d=180 mm (94) and 190 mm (98), respectively using the SEOL digital holography. FIG. 4(e) shows the sphacelaria's reconstructed image 102 at distance d=180 mm using phase-shifting on-line digital holography with two interferograms, and FIG. 4(f) is tribonema aequale's reconstructed image 106 at distance d=180 mm using SEOL digital holography. The experiments use a weak reference beam for the conjugate image, which overlaps the original image. As shown in FIG. 4(a)-4(f), the sharpest reconstructed image was obtained at distance d that is between 180 mm and 190 mm for both holographic methods. The reconstruction results indicate that focused images are obtained by the use of both, SEOL digital holography, as well as from the phase-shifting digital holography. This embodiment of the invention shows that SEOL digital holography may be a useful method for 3D biological object recognition because the conjugate image in the hologram contains information about the 3D biological object 2. In addition, SEOL digital holography can be performed on dynamic scenes without stringent environmental stability requirements.

3D Microorganism Reconstruction and Feature Extraction

Eight hologram samples from sphacelaria and tribonema aequale were generated to test the recognition performance of an embodiment of the invention. The eight sphacelaria samples are denoted as A1, . . . , A8 and the eight tribonema aequale samples are denoted as B1, . . . , B8. The position of the CCD during the experiments was changed resulting in different depths for the sharpest reconstruction image to test the robustness of the proposed algorithm. The samples A1-A3 are reconstructed at 180 mm, A4-A6 are reconstructed at 200 mm, and A7 and A8 are reconstructed at 300 mm and all samples of tribonema aequale (B1-B8) are reconstructed at 180 mm for the sharpest images.

Figure 5A:
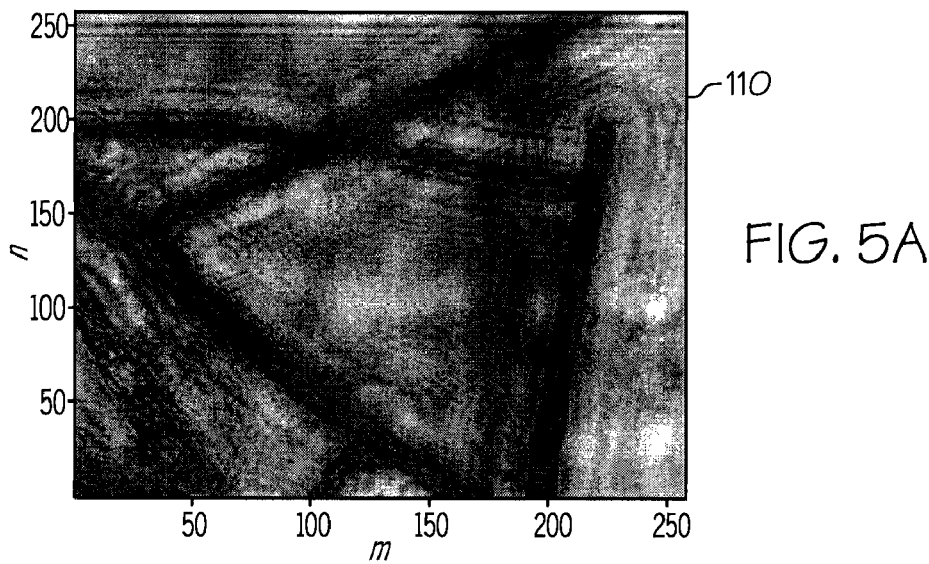
FIG. 5a depicts a reconstructed image (magnitude part) of a sphacelaria of sample A1 at d=180 mm.
Figure 5B:
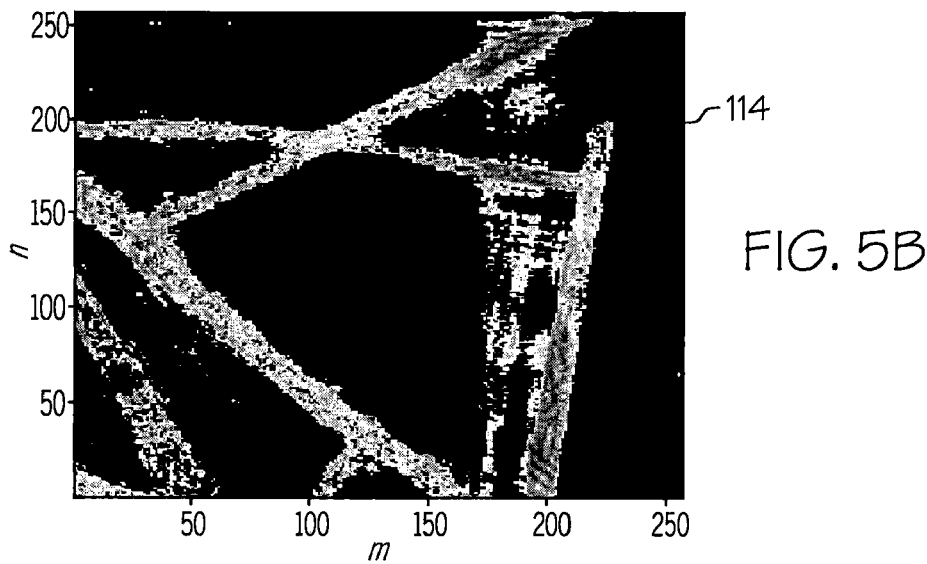
FIG. 5b depicts a segmented image (magnitude part) of a sphacelaria of sample A1.
Figure 5C:
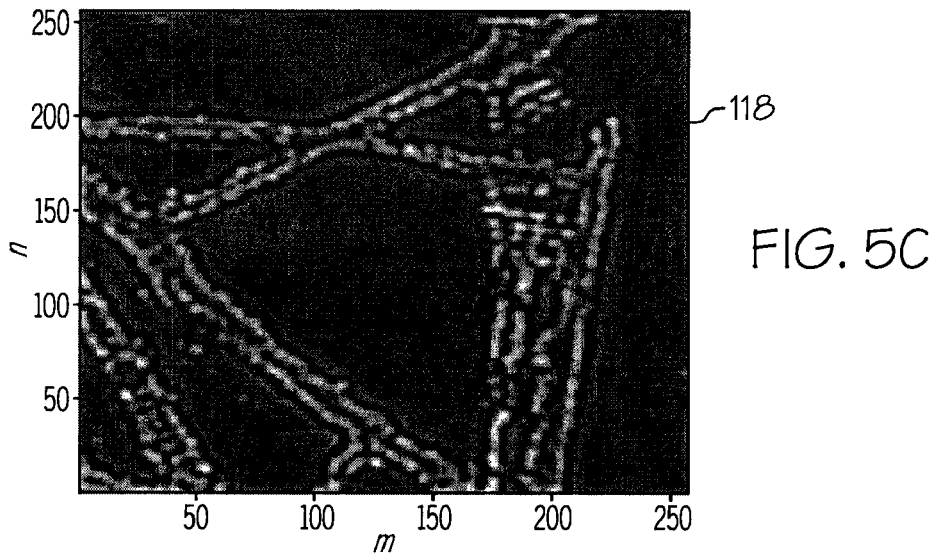
FIG. 5c depicts the real parts of Gabor coefficients in Section 4B when u=1.
Figure 5D:
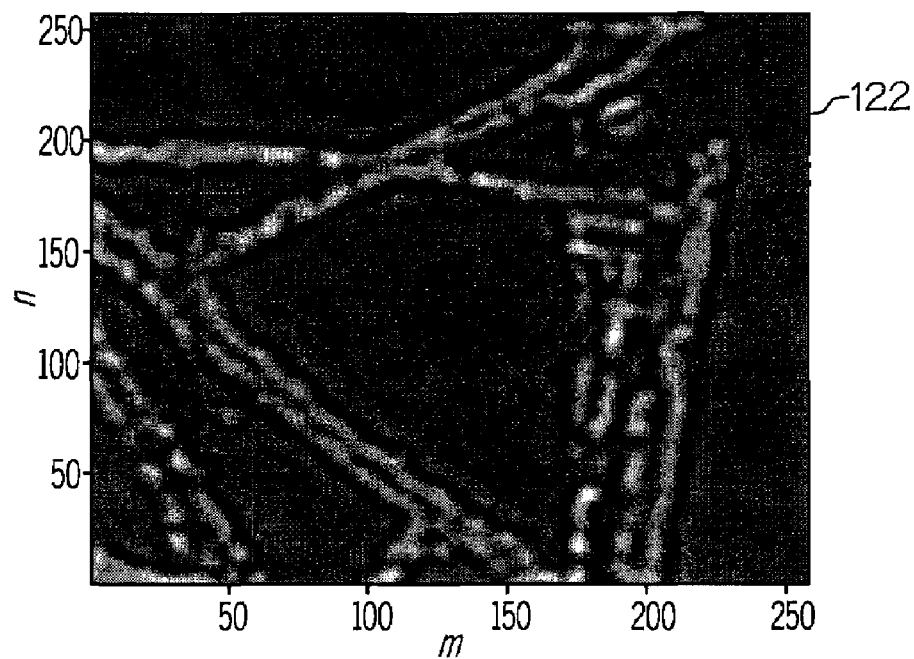
FIG. 5d depicts the real parts of Gabor coefficients in Section 4B when u=2.
Figure 5E:
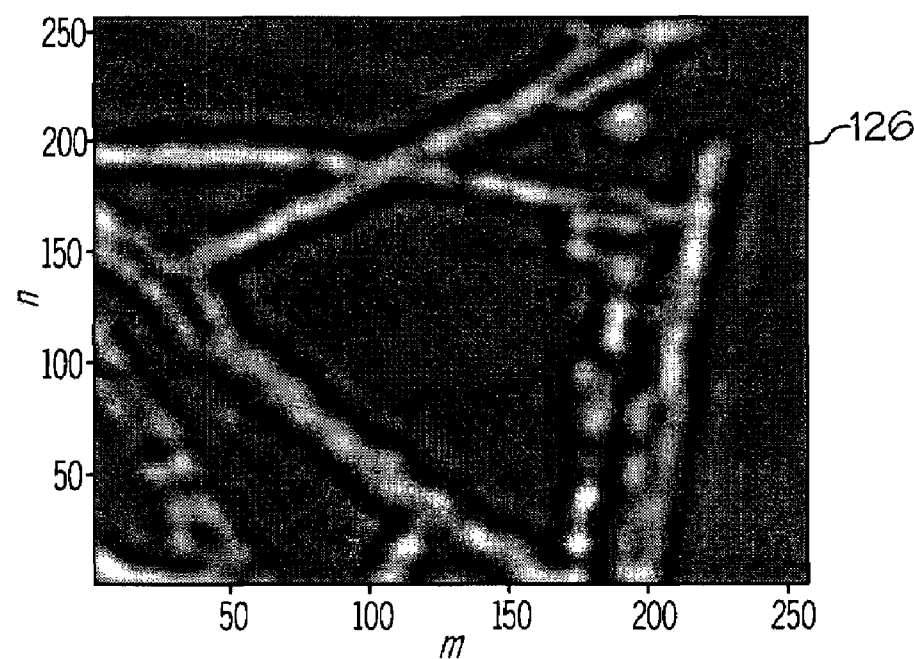
FIG. 5e depicts the real parts of Gabor coefficients in Section 4B when u=3.

Computationally reconstructed holographic images are cropped and reduced into an image with 256×256 pixels by the reduction ratio 0.25. The probability $P_s$ and the maximum transmission rate $r_{max}$ for the segmentation are set at 0.25 and 0.45, respectively. The assumption was made that microorganisms occupy less than 25% of lower intensity region and the intensity of microorganisms is less than 45% of the background diffraction field. FIGS. 5(a) and (b) show the reconstructed 110 and segmented 114 image of a sphacelaria sample (A1), respectively. FIGS. 5(c)-(e) show the real parts of Gabor coefficients in the section on Feature vector extraction above when u=1 (118), 2 (122), and 3 (126).

Two different reference graphs are selected and placed on the sample A1 and B1 to recognize two filamentous objects, which have different thicknesses and distributions. The results of the recognition process follow in the next subsections.

Recognition of Sphacelaria Alga

Figure 6A:
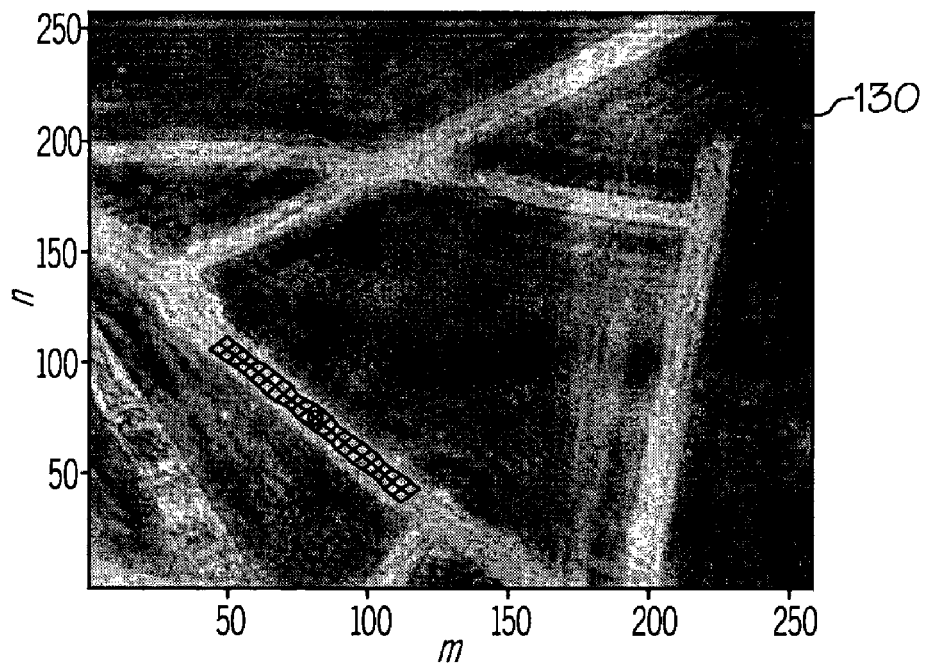
FIG. 6a depicts a reference image, with contrast reversal, of sample A1 with graph R.

A rectangular grid is selected as a reference graph for sphacelaria, which shows regular thickness in the reconstructed images. In this embodiment of the invention the reference graph is composed of 25×3 nodes and the distance between nodes is 4 pixels in the x and y directions. Therefore, the total number of nodes in the graph is 75. The reference graph R 130 is located in the sample A1 with $p_r=[81, 75]^t$ and $\theta_r=135°$ as shown in FIG. 6(a). To utilize the depth information, four reference images are used. They are reconstructed at d=170, 180, 190, and 200 mm, respectively. The threshold $\alpha_\Gamma$ and $\alpha_C$ are set at 0.65 and 1, respectively. Thresholds are selected heuristically to produce better results.

Considering the computational load, the graph S is translated by every 3 pixels in the x and y directions for measuring its similarity and difference with the graph R. To search the best matching angles, the graph S is rotated by 7.5° from 0 to 180° at every translated location. When the positions of rotated nodes are not integers, they are replaced with the nearest neighbor nodes.

Figure 6B:
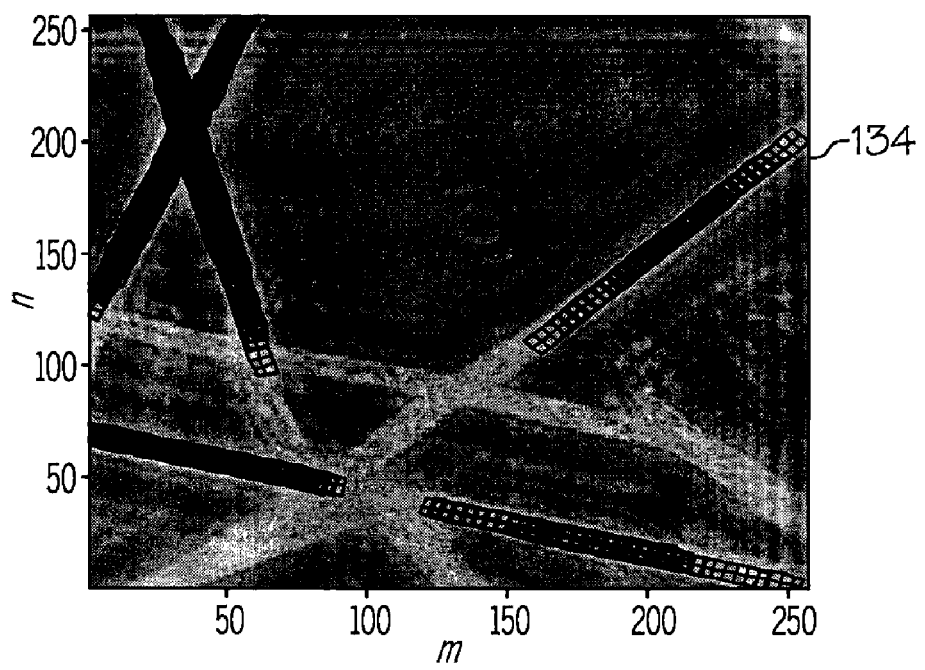
FIG. 6b depicts an image, with contrast reversal, with the RGM process of sample A8.
Figure 6C:
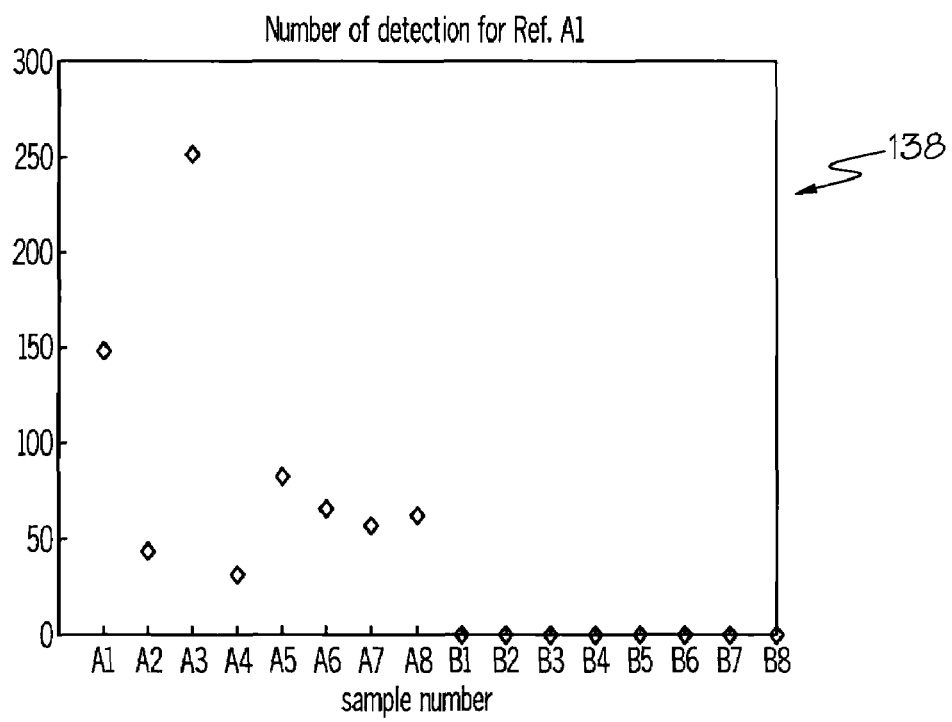
FIG. 6c graphs the number or detections for each sample relative to the reference sample A1.
Figure 6D:
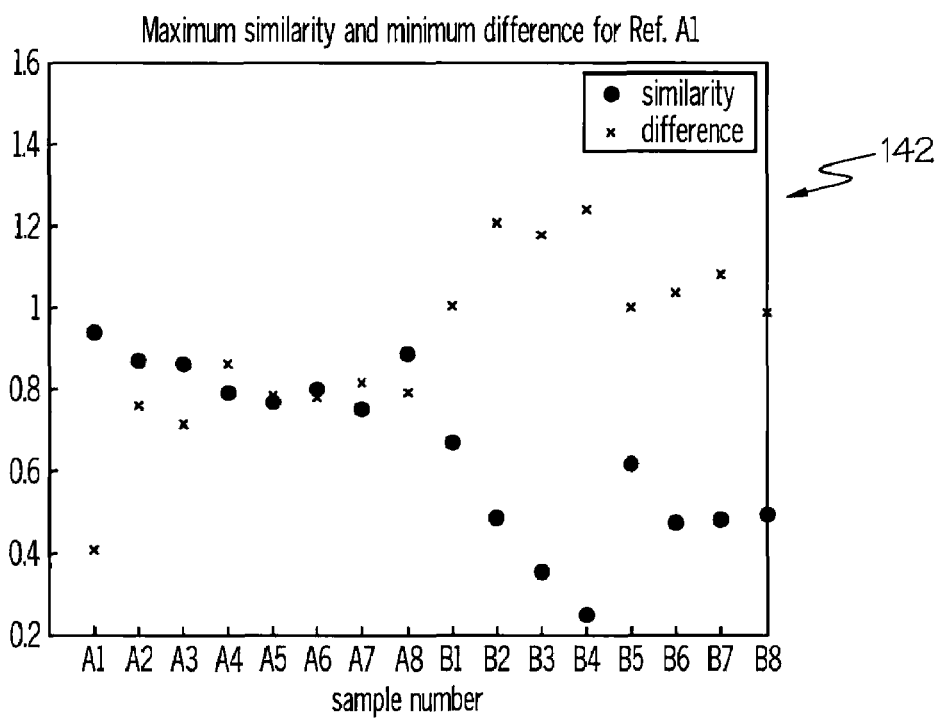
FIG. 6d graphs the maximum similarity and minimum difference cost for each sample relative to the reference sample A1.

FIG. 6(b) shows one sample (A8) 134 of test images with the RGM process. The reference shapes are detected 62 times along the filamentous objects. FIG. 6(c) 138 shows the number of detections for 16 samples. The detection number for A1-A8 varies from 31 to 251 showing strong similarity between the reference image (A1) and test images (A2-A8) of the same microorganism. There is no detection found in B11-B8. FIG. 6(d) 142 shows the maximum similarity and the minimum difference cost for all samples.

Recognition of Tribonema Aequale Alga

Figure 7A:
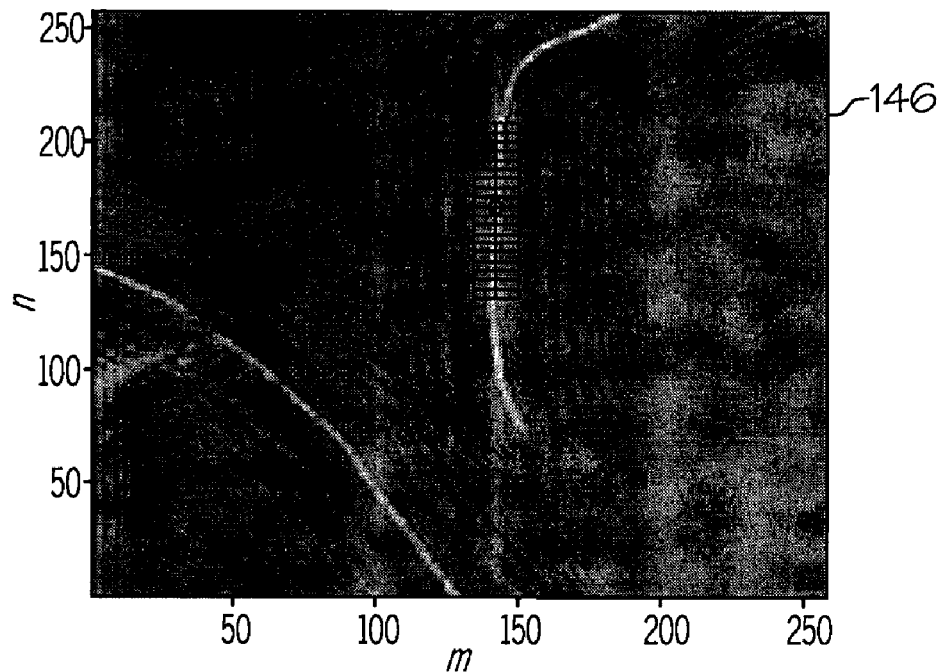
FIG. 7a depicts a reference image, with contrast reversal, of sample B1 with graph R.

To recognize tribonema aequale, a wider rectangular grid is selected to identify its thin filamentous structure. For this embodiment of the invention the reference graph is composed of 20×3 nodes and the distance between nodes is 4 pixels in x direction and 8 pixels in y direction, therefore, the total number of nodes in the graph is 60. The reference graph R 146 is located in the sample B1 with $p_r=[142, 171]^t$ and $\theta_r=90°$ as shown in FIG. 7(a). Four reference images are used which are reconstructed at d=170, 180, 190, and 200 mm, respectively. The threshold $\alpha_T$ and $\alpha_C$ are set at 0.8 and 0.65, respectively.

Figure 7B:
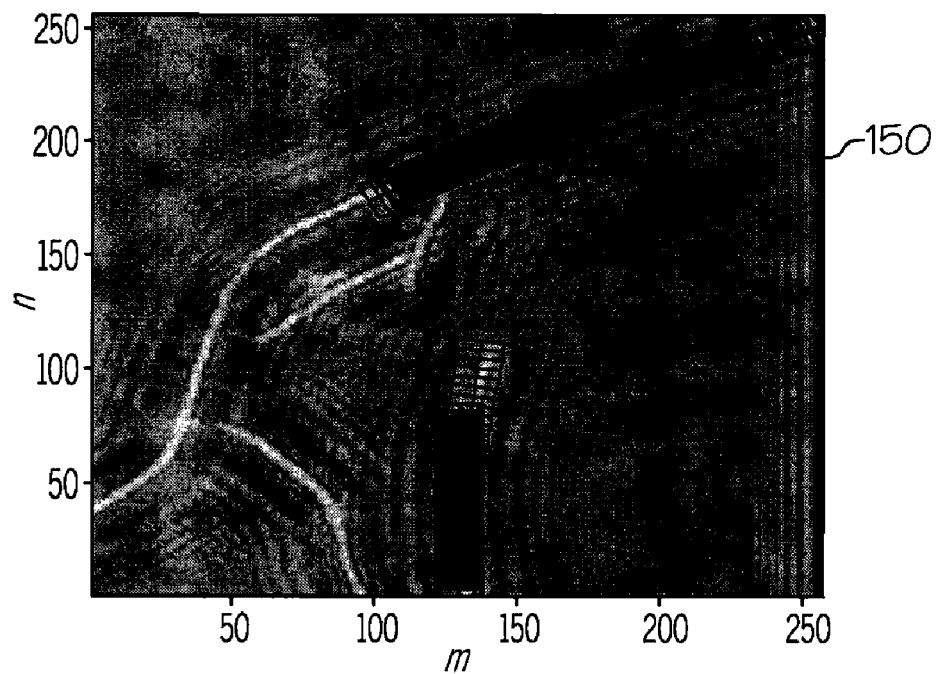
FIG. 7b depicts an image, with contrast reversal, with the RGM process of sample B2.
Figure 7C:
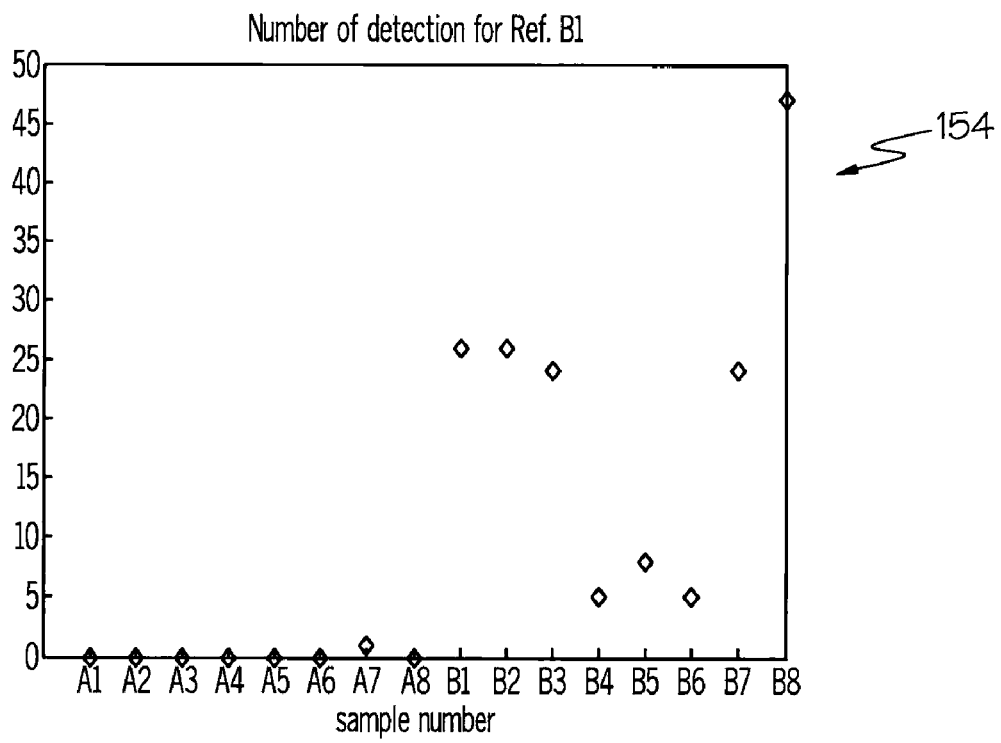
FIG. 7c graphs the number or detections for each sample relative to the reference sample B1.
Figure 7D:
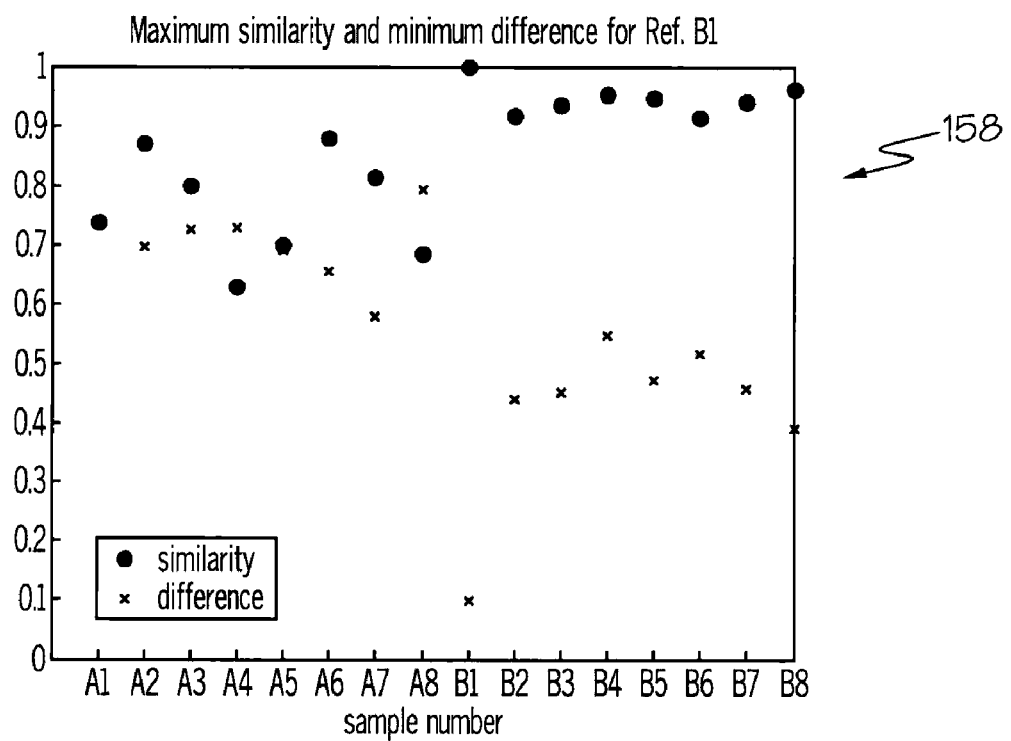
FIG. 7d graphs the maximum similarity and minimum difference cost for each sample relative to the reference sample B1.

FIG. 7(b) shows one sample (B2) 150 of test images with the RGM process. The reference shapes are detected 26 times along the thin filamentous object. FIG. 7(c) 154 shows the number of detections for 16 samples. The detection number for B1-B8 varies from 5 to 47. One false detection is found in the sample A7. FIG. 7(d) 158 shows the maximum similarity and the minimum difference cost for all samples. As a result, it is possible to recognize hologram samples of two different microorganisms by counting the number of detections of each reference shape.

For real-time application, computational complexity should be considered. For numerical reconstruction of the holographic image and Gabor filtering, the computational time of the algorithm is of the same order as the fast Fourier transformation (FFT) which is $O(N)=N \log_2 N$, where N is the total number of pixels in the holographic image. For the graph matching, the computational time depends on the shape and the size of the graph, the dimension of the feature vector, searching steps for the translation vector and the rotation angle. Since the largest operation is caused by searching the translation vector, that is $O(N)=N^2$, the proposed system requires quadratic computational complexity. Therefore, real-time processing can be achieved by developing parallel processing. Real-time operation is possible because SEOL holography requires a single exposure. Thus, with high speed electronics, it is possible to have real-time detection. This would not be possible with phase-shift holography, which requires multiple exposures.

This example has presented preliminary results for automatic real-time recognition of microorganisms by examining their 3D complex morphology. Three-dimensional visualization and recognition of microbiological objects by single-exposure on-line (SEOL) digital holography has been described. 3D imaging and recognition with SEOL digital holography is robust to movement of objects, and to environmental conditions during recording as compared with multiple exposure phase-shifting digital holography. Feature extraction is performed by segmentation and Gabor filtering. They are followed by a feature matching technique to localize specific shape features of two different microorganisms. The experimental results shown here detect the reference shapes in the unknown samples, however, they can be used for further training procedures. Indeed, several morphological traits can be combined to recognize different classes of microorganisms more efficiently.

Embodiments of the invention may have some of the following advantages: microorganisms are analyzed in 3D topology and coordinates, a single-exposure on-line computational holographic sensor allows optimization of the space bandwidth product for detection as well as robustness to environmental variations during the sensing process, only a single exposure is required, moving bacteria can be sensed within the time constant of the detector, various slices of the complex distribution of microorganism can be digitally reconstructed and numerically focused without mechanical focusing, 3D complex images are recorded and reconstructed in both magnitude and phase, complex amplitude of reconstructed holographic images are decomposed in the spatial frequency domain by Gabor-based wavelets to extract distinguishable features, and a pattern-matching technique measures the similarity of 3D geometrical shapes between a reference microorganism and an unknown sample.

One of ordinary skill in the art can appreciate that a computer or other client or server device can be deployed as part of a computer network, or in a distributed computing environment. In this regard, the methods and apparatus described above and/or claimed herein pertain to any computer system having any number of memory or storage units, and any number of applications and processes occurring across any number of storage units or volumes, which may be used in connection with the methods and apparatus described above and/or claimed herein. Thus, the same may apply to an environment with server computers and client computers deployed in a network environment or distributed computing environment, having remote or local storage. The methods and apparatus described above and/or claimed herein may also be applied to standalone computing devices, having programming language functionality, interpretation and execution capabilities for generating, receiving and transmitting information in connection with remote or local services.

The methods and apparatus described above and/or claimed herein is operational with numerous other general purpose or special purpose computing system environments or configurations. Examples of well known computing systems, environments, and/or configurations that may be suitable for use with the methods and apparatus described above and/or claimed herein include, but are not limited to, personal computers, server computers, hand-held or laptop devices, multiprocessor systems, microprocessor-based systems, network PCs, minicomputers, mainframe computers, distributed computing environments that include any of the above systems or devices.

The methods described above and/or claimed herein may be described in the general context of computer-executable instructions, such as program modules, being executed by a computer. Program modules typically include routines, programs, objects, components, data structures, etc. that perform particular tasks or implement particular abstract data types. Thus, the methods and apparatus described above and/or claimed herein may also be practiced in distributed computing environments such as between different units where tasks are performed by remote processing devices that are linked through a communications network or other data transmission medium. In a typical distributed computing environment, program modules and routines or data may be located in both local and remote computer storage media including memory storage devices. Distributed computing facilitates sharing of computer resources and services by direct exchange between computing devices and systems. These resources and services may include the exchange of information, cache storage, and disk storage for files. Distributed computing takes advantage of network connectivity, allowing clients to leverage their collective power to benefit the entire enterprise. In this regard, a variety of devices may have applications, objects or resources that may utilize the methods and apparatus described above and/or claimed herein.

Computer programs implementing the method described above will commonly be distributed to users on a distribution medium such as a CD-ROM. The program could be copied to a hard disk or a similar intermediate storage medium. When the programs are to be run, they will be loaded either from their distribution medium or their intermediate storage medium into the execution memory of the computer, thus configuring a computer to act in accordance with the methods and apparatus described above.

The term "computer-readable medium" encompasses all distribution and storage media, memory of a computer, and any other medium or device capable of storing for reading by a computer a computer program implementing the method described above.

Thus, the various techniques described herein may be implemented in connection with hardware or software or, where appropriate, with a combination of both. Thus, the methods and apparatus described above and/or claimed herein, or certain aspects or portions thereof, may take the form of program code or instructions embodied in tangible media, such as floppy diskettes, CD-ROMs, hard drives, or any other machine-readable storage medium, wherein, when the program code is loaded into and executed by a machine, such as a computer, the machine becomes an apparatus for practicing the methods and apparatus of described above and/or claimed herein. In the case of program code execution on programmable computers, the computing device will generally include a processor, a storage medium readable by the processor, which may include volatile and non-volatile memory and/or storage elements, at least one input device, and at least one output device. One or more programs that may utilize the techniques of the methods and apparatus described above and/or claimed herein, e.g., through the use of a data processing, may be implemented in a high level procedural or object oriented programming language to communicate with a computer system. However, the program(s) can be implemented in assembly or machine language, if desired. In any case, the language may be a compiled or interpreted language, and combined with hardware implementations.

The methods and apparatus described above and/or claimed herein may also be practiced via communications embodied in the form of program code that is transmitted over some transmission medium, such as over electrical wiring or cabling, through fiber optics, or via any other form of transmission, wherein, when the program code is received and loaded into and executed by a machine, such as an EPROM, a gate array, a programmable logic device (PLD), a client computer, or a receiving machine having the signal processing capabilities as described in exemplary embodiments above becomes an apparatus for practicing the method described above and/or claimed herein. When implemented on a general-purpose processor, the program code combines with the processor to provide a unique apparatus that operates to invoke the functionality of the methods and apparatus described above and/or claimed herein. Further, any storage techniques used in connection with the methods and apparatus described above and/or claimed herein may invariably be a combination of hardware and software.

The operations and methods described herein may be capable of or configured to be or otherwise adapted to be performed in or by the disclosed or described structures.

While the methods and apparatus described above and/or claimed herein have been described in connection with the preferred embodiments and the figures, it is to be understood that other similar embodiments may be used or modifications and additions may be made to the described embodiment for performing the same function of the methods and apparatus described above and/or claimed herein without deviating there from. Furthermore, it should be emphasized that a variety of computer platforms, including handheld device operating systems and other application specific operating systems are contemplated, especially given the number of wireless networked devices in use.

While the description above refers to particular embodiments, it will be understood that many modifications may be made without departing from the spirit thereof. The accompanying claims are intended to cover such modifications as would fall within the true scope and spirit of the present invention.

What is claimed is:

1. A method of identifying a microorganism, comprising:
diffracting laser light through a microorganism;
combining a reference beam with the diffracted light on a single axis;
recording the combined light holographically as a three-dimensional image with a single exposure on a detector array;
reconstructing the holographic image; and
matching the reconstructed image with reference images of known microorganisms.

2. The method of claim 1, further comprising:
splitting light from a single laser to form the reference beam and the light that is diffracted through the microorganism.

3. The method of claim 1, further comprising:
exposing the microorganism by diffracting laser light through the microorganism with an interferometer; and
opto-electronically recording the complex amplitude distribution generated by the diffraction at a single plane.

4. The method of claim 1, wherein:
The recording is of a single exposure with a charged coupled device (CCD) sensor.

5. The method of claim 1, further comprising:
magnifying optically the microorganism image to be recorded.

6. The method of claim 1, wherein:
the reconstructing of the image is performed computationally.

7. The method of claim 1, wherein:
the reconstructing of the image is performed at various depths.

8. The method of claim 1, further comprising:
segmenting foreground features with histogram analysis.

9. The method of claim 1, further comprising:
extracting salient features via signal processing.

10. The method of claim 1, wherein:
the matching of the reconstructed image with images of known microorganisms is done with rigid graph matching (RGM).

11. The method of claim 1, wherein:
the matching comprises comparing the reconstructed image to images of known microorganisms; and selecting the known microorganism image that has a maximum of similarities or a minimum of differences.

12. The method of claim 1, wherein:
the matching comprises combining rigid graph matching (RGM) with Gabor-based wavelets for the complex images in a template matching technique that is invariant to shift, rotation and distortion.

13. A method of recognizing a microorganism, comprising:
recording three-dimensional complex morphologies of a microorganism with single-exposure on-line (SEOL) digital holography;
reconstructing the recorded image digitally; and matching the reconstructed three-dimensional complex morphologies with three-dimensional complex morphologies of known microorganisms.

14. An apparatus for identifying a microorganism, comprising:
   an interferometer to record an image of an unknown microorganism using single-exposure on-line (SEOL) digital holography;
   a means for reconstructing the recorded image; and
   a means for matching the reconstructed image with images of known microorganism.

15. The apparatus of claim 14, further comprising: a means for magnifying optically the microorganism image being recorded.

16. The apparatus of claim 14, further comprising: a means for reconstructing the complex amplitude image at any depth plane.

17. The apparatus of claim 14, further comprising: a means for segmenting foreground objects.

18. The apparatus of claim 14, further comprising: a means for extracting salient features.

19. A computer program product for identifying an image of a microorganism in a computer environment, the computer program product comprising a storage medium readable by a processing circuit and storing instructions for execution by the processing circuit for facilitating a method comprising:
   receiving an image of a microorganism from a detector array of a single-exposure on-line (SEOL) digital holography system;
   digitally storing the image;
   reconstructing the image digitally; and
   matching the reconstructed image with reference images of known microorganisms.

20. The method of claim 19, wherein:
   the matching uses a rigid graph matching (RGM) technique to match three-dimensional (3-D) complex morphologies of the unknown microorganism with 3-D complex morphologies of the known microorganism.

* * * * *